(12) United States Patent
Denk et al.

(10) Patent No.: US 10,441,246 B2
(45) Date of Patent: Oct. 15, 2019

(54) FAST VOLUME CONTRAST IMAGING (VCI-C) AND OMNIVIEW ACQUISITION

(71) Applicant: General Electric Company, Schenectady, NY (US)

(72) Inventors: Stefan Denk, Ried im Innkreis (AT); Harald Deischinger, Schlatt (AT)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 319 days.

(21) Appl. No.: 15/380,477

(22) Filed: Dec. 15, 2016

(65) Prior Publication Data
US 2018/0168543 A1 Jun. 21, 2018

(51) Int. Cl.
| | |
|---|---|
| *A61B 8/14* | (2006.01) |
| *A61B 8/08* | (2006.01) |
| *A61B 8/00* | (2006.01) |
| *G01S 7/52* | (2006.01) |
| *G01S 15/89* | (2006.01) |

(52) U.S. Cl.
CPC ............ *A61B 8/145* (2013.01); *A61B 8/5207* (2013.01); *A61B 8/54* (2013.01); *G01S 7/52084* (2013.01); *G01S 7/52085* (2013.01); *G01S 15/8913* (2013.01); *G01S 15/8915* (2013.01); *G01S 15/8927* (2013.01); *A61B 8/4444* (2013.01); *A61B 8/4488* (2013.01); *A61B 8/461* (2013.01); *A61B 8/469* (2013.01)

(58) Field of Classification Search
USPC .......................................................... 600/447
See application file for complete search history.

(56) References Cited

U.S. PATENT DOCUMENTS

| | | | | |
|---|---|---|---|---|
| 8,002,705 | B1 * | 8/2011 | Napolitano | G01S 7/52019 600/407 |
| 2004/0159155 | A1 * | 8/2004 | Ogasawara | A61B 5/08 73/633 |
| 2014/0147013 | A1 * | 5/2014 | Shandas | A61B 8/481 382/107 |

* cited by examiner

*Primary Examiner* — Nicole F Lavert
(74) *Attorney, Agent, or Firm* — McAndrews, Held & Malloy, Ltd.; Jacob Groethe; David Bates

(57) ABSTRACT

Systems and methods are provided for fast volume contrast imaging in C-plane (VCI-C) and Omniview acquisition.

21 Claims, 5 Drawing Sheets

FAST VOLUME CONTRAST IMAGING (VCI-C) AND OMNIVIEW ACQUISITION

FIELD

Aspects of the present disclosure relate to medical imaging. More specifically, certain embodiments relate to methods and systems for fast volume contrast imaging in C-plane (VCI-C) and Omniview acquisition.

BACKGROUND

Various medical imaging techniques may be used, such as in imaging organs and soft tissues in a human body. Examples of medical imaging techniques include ultrasound imaging, computed tomography (CT) scans, magnetic resonance imaging (MRI), etc. The manner by which images are generated during medical imaging depends on the particular technique.

For example, ultrasound imaging uses real time, non-invasive high frequency sound waves to produce ultrasound images, typically of organs, tissues, objects (e.g., fetus) inside the human body. Images produced or generated during medical imaging may be two-dimensional (2D), three-dimensional (3D), and/or four-dimensional (4D) images (essentially real-time/continuous 3D images). During medical imaging, imaging datasets (including, e.g., volumetric imaging datasets during 3D/4D imaging) are acquired and used in generating and rendering corresponding images (e.g., via a display) in real-time.

Conventional and traditional approaches may, however, have some drawbacks and/or shortcomings. For example, conventional systems and methods may be inefficient—e.g., suffering from rather low speed of acquisition of ultrasound echoes, particularly with respect to certain modes of ultrasound imaging.

Further limitations and disadvantages of conventional and traditional approaches will become apparent to one of skill in the art, through comparison of such systems with some aspects of the present disclosure, as set forth in the remainder of the present application with reference to the drawings.

BRIEF SUMMARY

System and methods are provided for fast volume contrast imaging in C-plane (VCI-C) and Omniview acquisition, substantially as shown in and/or described in connection with at least one of the figures, as set forth more completely in the claims.

These and other advantages, aspects and novel features of the present disclosure, as well as details of one or more illustrated example embodiments thereof, will be more fully understood from the following description and drawings.

DETAILED DESCRIPTION

Figure 1:
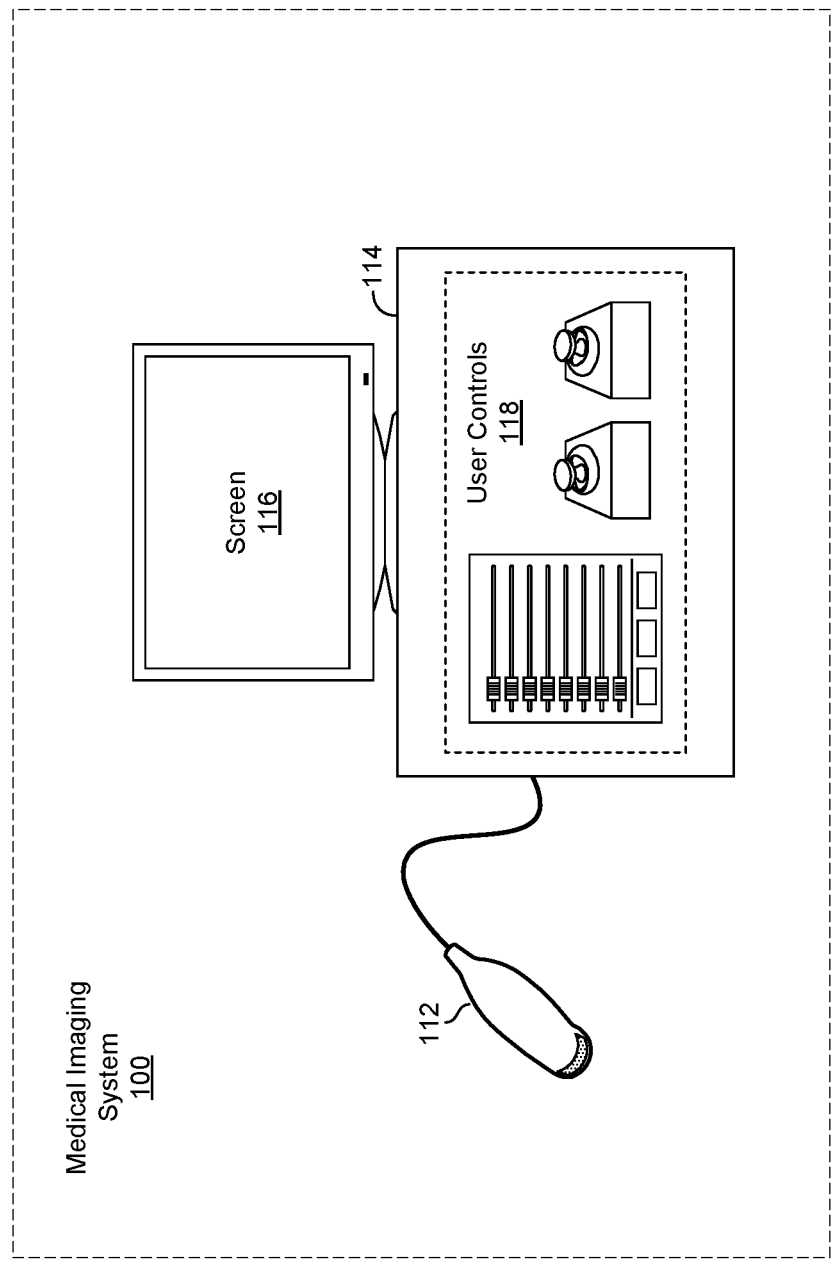
FIG. 1 is a block diagram illustrating an example medical imaging system that supports fast volume contrast imaging in C-plane (VCI-C) and Omniview acquisition.

Various implementations in accordance with the present disclosure may be directed to fast volume contrast imaging in C-plane (VCI-C) and Omniview acquisition.

An example ultrasound system in accordance with the present disclosure may comprise a probe that may be operable to transmit ultrasound signals and receive echo ultrasound signals; and processing circuitry that may be operable to increase acquisition speed during one or more particular ultrasound imaging modes by: dividing an area subject to transmittal of ultrasound signals, and capture of corresponding echo ultrasound signals, by the ultrasound probe into a plurality of sectors; triggering transmitting of one or more beams in a first one of the plurality of sectors; and triggering transmittal of one or more beams in at least a second one of the plurality of sectors. Each of the one or more beams transmitted in the second one of the plurality of sectors is triggered such that it is transmitted after transmitting of a corresponding beam in the first one of the plurality of sectors and before echo of the corresponding beam in the first one of the plurality of sectors is received. The one or more particular ultrasound imaging modes may comprise volume contrast imaging in C-plane (VCI-C) and Omniview.

In an example implementation, the processing circuitry may be operable to determine a timing delay between transmittal of each beam in the first one of the plurality of sectors and reception of an echo of the beam; and determine, based on the determined timing delay and number of sectors in the plurality of sectors, a timing shift for transmitting a corresponding beam on at least the second one of the plurality of sectors. The processing circuitry may be operable to determine the timing delay based on speed of sound and a particular distance associated with a desired region of interest (ROI), such as a thickness of the ROI and/or a maximum depth of the ROI.

In an example implementation, the processing circuitry may be operable to configure the plurality of sectors such that beams transmitted in each of the plurality of sectors are spatially separated in relation to one another.

In an example implementation, the processing circuitry may be operable to configure the plurality of sectors based on geometric characteristics of the ultrasound probe. The geometric characteristics may comprise one or more of size, shape, and curvature.

An example method in accordance with the present disclosure may increase acquisition speed, in an ultrasound device, during one or more particular ultrasound imaging modes by dividing an area, subject to transmittal of ultrasound signals and capture of corresponding echo ultrasound signals by an ultrasound probe, into a plurality of sectors; triggering transmitting of one or more beams in a first one of the plurality of sectors; and triggering transmittal of one or more beams in at least a second one of the plurality of sectors. Each of the one or more beams transmitted in the second one of the plurality of sectors is triggered such that it is transmitted after transmitting of a corresponding beam in the first one of the plurality of sectors and before echo of the corresponding beam in the first one of the plurality of sectors is received. The one or more particular ultrasound imaging modes may comprise volume contrast imaging in C-plane (VCI-C) and Omniview.

In an example implementation, the method may comprise determining a timing delay between transmittal of each beam in the first one of the plurality of sectors and reception of an echo of the beam; and determining, based on the determined timing delay and a number of sectors in the plurality of sectors, a timing shift for transmitting a corresponding beam in at least the second one of the plurality of sectors. The timing delay may be determined based on speed of sound and a particular distance associated with a desired region of interest (ROI), such as a thickness of the ROI and/or a maximum depth of the ROI.

In an example implementation, the method may comprise configuring the plurality of sectors such that beams transmitted in each of the plurality of sectors are spatially separated in relation to one another.

In an example implementation, the method may comprise configuring the plurality of sectors based on geometric characteristics of the ultrasound probe. The geometric characteristics may comprise one or more of size, shape, and curvature.

An example non-transitory computer readable medium, in accordance with the present disclosure, may have stored thereon a computer program having at least one code section, the at least one code section being executable in an ultrasound device for causing the ultrasound device to increase acquisition speed, during one or more particular ultrasound imaging modes, by performing one or more steps that comprise: dividing an area, subject to transmittal of ultrasound signals and capture of corresponding echo ultrasound signals by an ultrasound probe, into a plurality of sectors; triggering transmitting of one or more beams in a first one of the plurality of sectors; and triggering transmittal of one or more beams in at least a second one of the plurality of sectors. Each of the one or more beams transmitted in the second one of the plurality of sectors is triggered such that it is transmitted after transmitting of a corresponding beam in the first one of the plurality of sectors and before echo of the corresponding beam in the first one of the plurality of sectors is received. The one or more particular ultrasound imaging modes may comprise volume contrast imaging in C-plane (VCI-C) and Omniview.

In an example implementation, the one or more steps performed in the ultrasound device may comprise determining a timing delay between transmittal of each beam in the first one of the plurality of sectors and reception of an echo of the beam; and determining, based on the determined timing delay and a number of sectors in the plurality of sectors, a timing shift for transmitting a corresponding beam in at least the second one of the plurality of sectors. The timing delay may be determined based on speed of sound and a particular distance associated with a desired region of interest (ROI), such as a thickness of the ROI and/or a maximum depth of the ROI.

In an example implementation, the one or more steps performed in the ultrasound device may comprise configuring the plurality of sectors such that beams transmitted in each of the plurality of sectors are spatially separated in relation to one another.

In an example implementation, the one or more steps performed in the ultrasound device may comprise configuring the plurality of sectors based on geometric characteristics of the ultrasound probe. The geometric characteristics may comprise one or more of size, shape, and curvature.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present invention is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an embodiment," "one embodiment," "a representative embodiment," "an example embodiment," "various embodiments," "certain embodiments," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

In addition, as used herein, the phrase "pixel" also includes embodiments where the data is represented by a "voxel." Thus, both the terms "pixel" and "voxel" may be used interchangeably throughout this document.

Also as used herein, the term "image" broadly refers to both viewable images and data representing a viewable image. However, many embodiments generate (or are configured to generate) at least one viewable image. Further, with respect to ultrasound imaging, as used herein the phrase "image" is used to refer to an ultrasound mode such as B-mode, CF-mode and/or sub-modes of CF such as TVI, Angio, B-flow, BMI, BMI_Angio, and in some cases also MM, CM, PW, TVD, CW where the "image" and/or "plane" includes a single beam or multiple beams.

Furthermore, the term processor or processing unit, as used herein, refers to any type of processing unit that can carry out the required calculations, such as single or multi-core: CPU, Graphics Board, DSP, FPGA, ASIC, or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams." Also, forming of images may be performed using channel combinations that may originate from more than one transmit event (e.g., synthetic aperture techniques).

In various embodiments, imaging processing, including visualization enhancement, to form images may be performed, for example, in software, firmware, hardware, or a combination thereof.

FIG. 1 is a block diagram illustrating an example medical imaging system that supports fast volume contrast imaging in C-plane (VCI-C) and Omniview acquisition. Shown in FIG. 1 is an example medical imaging system 100.

The medical imaging system 100 comprise suitable hardware, software, or a combination thereof, for supporting medical imaging—that is enabling obtaining data used in generating and/or rendering images during medical imaging exams. This may entail capturing of particular type of data, in particular manner, which may in turn be used in generating data for the images. For example, the medical imaging system 100 may be an ultrasound system, configured for generating and/or rendering ultrasound images. An example implementation of an ultrasound system that may correspond to the medical imaging system 100 is described in more detail with respect to FIG. 2.

As shown in FIG. 1, the medical imaging system 100 may comprise a probe 112, which may be portable and movable, and a display/control unit 114. The probe 112 may be used in generating and/or capturing particular type of signals (or data corresponding thereto), such as by being moved over a patient's body (or part thereof). For example, where the medical imaging system 100 is an ultrasound system, the probe 112 may emit ultrasound signals and capture echo ultrasound images.

The display/control unit 114 may be used in displaying images (e.g., via a screen 116). Further, the display/control unit 114 may also support user input/output. For example, the display/control unit 114 may provide (e.g., via the screen 116), in addition to the images, user feedback (e.g., information relating to the system, functions thereof, settings thereof, etc.). The display/control unit 114 may also support user input (e.g., via user controls 118), such as to allow controlling of the medical imaging. The user input may be directed to controlling display of images, selecting settings, specifying user preferences, requesting feedback, etc.

In operation, the medical imaging system 100 may be used in generating and presenting (e.g., rendering or displaying) images during medical exams, and/or in supporting user input/output in conjunction therewith. The images may be 2D, 3D, and/or 4D images. The particular operations or functions performed in the medical imaging system 100 to facilitate the generating and/or presenting of images depends on the type of system—that is the manner by which the data corresponding to the images is obtained and/or generated. For example, in ultrasound imaging, the data is based on emitted and echo ultrasound signals, as described in more detail with respect to FIG. 2.

In various implementations in accordance with the present disclosure, medical imaging systems (such as, e.g., the medical imaging system 100) may be improved, such as by increasing speed of obtaining medical images. For example, in instances where the medical imaging system 100 comprises ultrasound imaging system, the speed of acquisition of echo ultrasound signals may be increased, such is by shortening delays between transmissions of ultrasound beams. This may be particularly done in certain acquisition modes, such as volume contrast imaging in the C-plane (VCI-C) and Omniview (as well as other acquisition modes). In modes such as VCI-C imaging is based on real-time acquisition of volumetric data (based on echo signals) for enabling rendering a defined thick slice portion in the coronal direction—thus, modes of operations such as VCI-C provide scan planes not accessible by conventional B-mode scanning. With such modes, speed of acquisition may be increased by, e.g., acquiring data only for depth needed (depth of plane), therefore enabling a temporal overlapping of multiple acquisition beams. This is described in more detail below.

Figure 2:
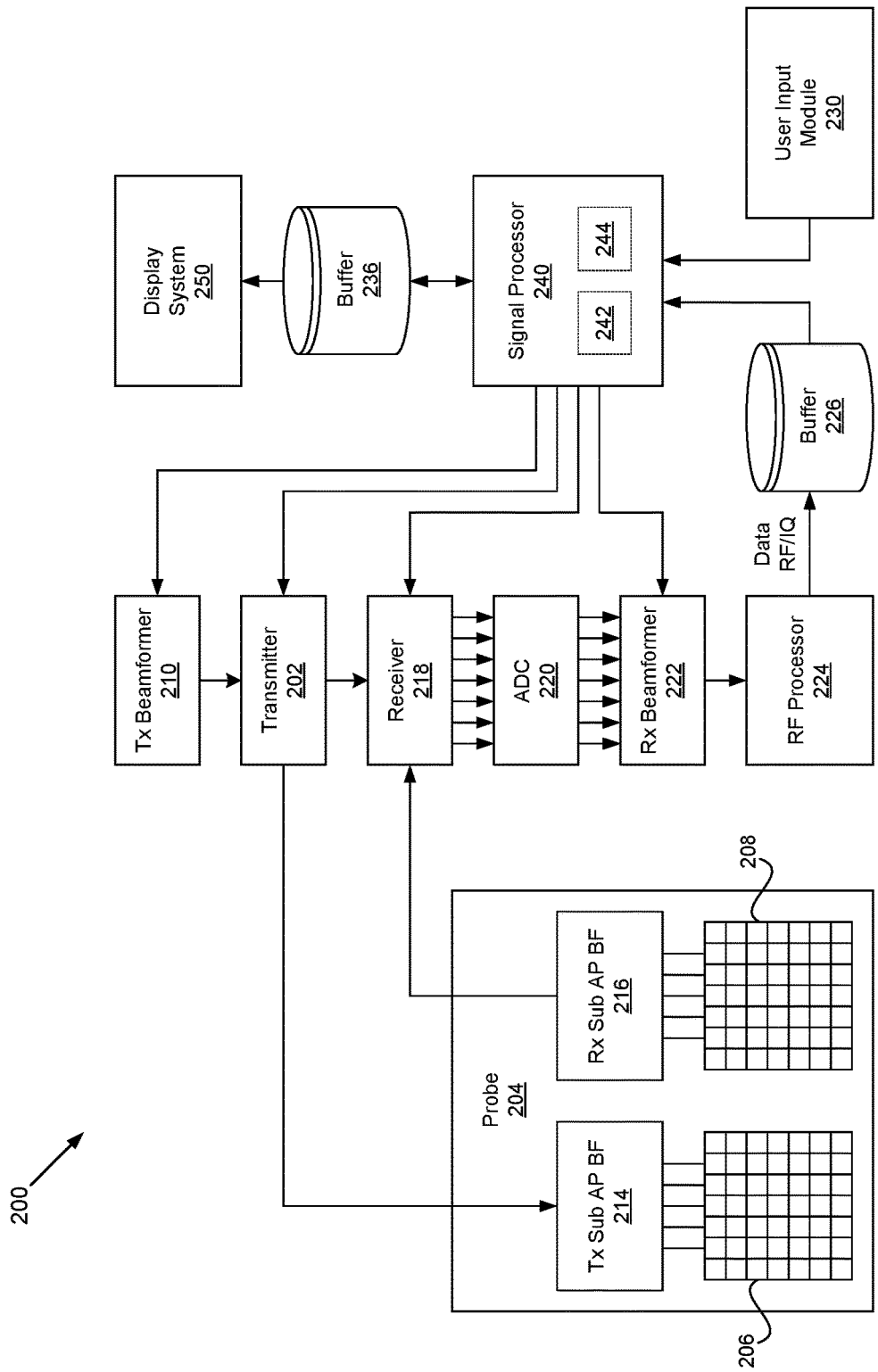
FIG. 2 is a block diagram illustrating an example ultrasound system that supports fast volume contrast imaging in C-plane (VCI-C) and Omniview acquisition.

FIG. 2 is a block diagram illustrating an example ultrasound that supports fast volume contrast imaging in C-plane (VCI-C) and Omniview acquisition. Shown in FIG. 2 is an ultrasound system 200.

The ultrasound system 200 may comprise suitable components (physical devices, circuitry, etc.) for providing ultrasound imaging. The ultrasound system 200 may correspond to the medical imaging system 100 of FIG. 1 in ultrasound imaging use scenarios. The ultrasound system 200 comprises, for example, a transmitter 202, an ultrasound probe 204, a transmit beamformer 210, a receiver 218, a receive beamformer 222, a RF processor 224, a RF/IQ buffer 226, a user input module 230, a signal processor 240, an image buffer 236, and a display system 250.

The transmitter 202 may comprise suitable circuitry that may be operable to drive the ultrasound probe 204. The transmitter 202 and the ultrasound probe 204 may be implemented and/or configured for one-dimensional (1D), two-dimensional (2D), three-dimensional (3D), and/or four-dimensional (4D) ultrasound scanning. The ultrasound probe 204 may comprise a one-dimensional (1D, 1.25D, 1.5D, and 1.75D) array or a two-dimensional (2D) array of piezoelectric elements. For example, as shown in FIG. 2, the ultrasound probe 204 may comprise a group of transmit transducer elements 206 and a group of receive transducer elements 208, that normally constitute the same elements. The transmitter 202 may be driven by the transmit beamformer 210.

The transmit beamformer 210 may comprise suitable circuitry that may be operable to control the transmitter 202 which, through a transmit sub-aperture beamformer 214, drives the group of transmit transducer elements 206 to emit ultrasonic transmit signals into a region of interest (e.g., human, animal, underground cavity, physical structure and the like). In this regard, the group of transmit transducer elements 206 can be activated to transmit ultrasonic signals. The ultrasonic signals may comprise, for example, pulse sequences that are fired repeatedly at a pulse repetition frequency (PRF), which may typically be in the kilohertz range. The pulse sequences may be focused at the same transmit focal position with the same transmit characteristics. A series of transmit firings focused at the same transmit focal position may be referred to as a "packet."

The transmitted ultrasonic signals may be back-scattered from structures in the object of interest, like tissue, to produce echoes. The echoes are received by the receive transducer elements 208. The group of receive transducer elements 208 in the ultrasound probe 204 may be operable to convert the received echoes into analog signals, undergo sub-aperture beamforming by a receive sub-aperture beamformer 216 and are then communicated to the receiver 218.

The receiver 218 may comprise suitable circuitry that may be operable to receive and demodulate the signals from the probe transducer elements or receive sub-aperture beamformer 216. The demodulated analog signals may be communicated to one or more of the plurality of A/D converters (ADCs) 220.

Each plurality of A/D converters 220 may comprise suitable circuitry that may be operable to convert analog signals to corresponding digital signals. In this regard, the plurality of A/D converters 220 may be configured to convert demodulated analog signals from the receiver 218 to corresponding digital signals. The plurality of A/D converters 220 are disposed between the receiver 218 and the receive beamformer 222. Notwithstanding, the disclosure is not limited in this regard. Accordingly, in some embodiments, the plurality of A/D converters 220 may be integrated within the receiver 218.

The receive beamformer 222 may comprise suitable circuitry that may be operable to perform digital beamforming processing to, for example, sum the delayed channel signals received from the plurality of A/D converters 220 and output a beam summed signal. The resulting processed information may be converted back to corresponding RF signals. The corresponding output RF signals that are output from the receive beamformer 222 may be communicated to the RF processor 224. In accordance with some embodiments, the receiver 218, the plurality of A/D converters 220, and the beamformer 222 may be integrated into a single beamformer, which may be digital. In some instances, a software beamformer may be utilized, with both input and output configured as In-phase and quadrature (IQ) pairs.

The RF processor 224 may comprise suitable circuitry that may be operable to demodulate the RF signals. In some instances, the RF processor 224 may comprise a complex demodulator (not shown) that is operable to demodulate the RF signals to form In-phase and quadrature (IQ) data pairs (e.g., B-mode data pairs) which may be representative of the corresponding echo signals. The RF (or IQ) signal data may then be communicated to an RF/IQ buffer 226.

The RF/IQ buffer 226 may comprise suitable circuitry that may be operable to provide temporary storage of output of the RF processor 224—e.g., the RF (or IQ) signal data, which is generated by the RF processor 224.

The user input module 230 may comprise suitable circuitry that may be operable to enable obtaining or providing input to the ultrasound system 200, for use in operations thereof. For example, the user input module 230 may be used to input patient data, surgical instrument data, scan parameters, settings, configuration parameters, change scan mode, and the like. In an example embodiment, the user input module 230 may be operable to configure, manage and/or control operation of one or more components and/or modules in the ultrasound system 200. In this regard, the user input module 230 may be operable to configure, manage and/or control operation of transmitter 202, the ultrasound probe 204, the transmit beamformer 210, the receiver 218, the receive beamformer 222, the RF processor 224, the RF/IQ buffer 226, the user input module 230, the signal processor 240, the image buffer 236, and/or the display system 250.

The signal processor 240 may comprise suitable circuitry that may be operable to process the ultrasound scan data (e.g., the RF and/or IQ signal data) and/or to generate corresponding ultrasound images, such as for presentation on the display system 250. The signal processor 240 is operable to perform one or more processing operations according to a plurality of selectable ultrasound modalities on the acquired ultrasound scan data. In some instances, the signal processor 240 may be operable to perform compounding, motion tracking, and/or speckle tracking. Acquired ultrasound scan data may be processed in real-time—e.g., during a B-mode scanning session, as the B-mode echo signals are received. Additionally or alternatively, the ultrasound scan data may be stored temporarily in the RF/IQ buffer 226 during a scanning session and processed in less than real-time in a live or off-line operation.

In operation, the ultrasound system 200 may be used in generating ultrasonic images, including two-dimensional (2D), three-dimensional (3D), and/or four-dimensional (4D) images. In this regard, the ultrasound system 200 may be operable to continuously acquire ultrasound scan data at a particular frame rate, which may be suitable for the imaging situation in question. For example, frame rates may range from 20-70 but may be lower or higher. The acquired ultrasound scan data may be displayed on the display system 250 at a display-rate that can be the same as the frame rate, or slower or faster. An image buffer 236 is included for storing processed frames of acquired ultrasound scan data that are not scheduled to be displayed immediately. Preferably, the image buffer 236 is of sufficient capacity to store at least several seconds' worth of frames of ultrasound scan data. The frames of ultrasound scan data are stored in a manner to facilitate retrieval thereof according to its order or time of acquisition. The image buffer 236 may be embodied as any known data storage medium.

In some instances, the ultrasound system 200 may be configured to support grayscale and color based operations. For example, the signal processor 240 may be operable to perform grayscale B-mode processing and/or color processing. The grayscale B-mode processing may comprise processing B-mode RF signal data or IQ data pairs. For example, the grayscale B-mode processing may enable forming an envelope of the beam-summed receive signal by computing the quantity $(I^2+Q^2)^{1/2}$. The envelope can undergo additional B-mode processing, such as logarithmic compression to form the display data. The display data may be converted to X-Y format for video display. The scan-converted frames can be mapped to grayscale for display. The B-mode frames that are provided to the image buffer 236 and/or the display system 250. The color processing may comprise processing color based RF signal data or IQ data pairs to form frames to overlay on B-mode frames that are provided to the image buffer 236 and/or the display system 250. The grayscale and/or color processing may be adaptively adjusted based on user input—e.g., a selection from the user input module 230, for example, for enhance of grayscale and/or color of particular area.

In some instances, ultrasound imaging may include generation and/or display of volumetric ultrasound images—that is where objects (e.g., organs, tissues, etc.) are displayed three-dimensional 3D. In this regard, with 3D (and similarly 4D) imaging, volumetric ultrasound datasets may be acquired, comprising voxels that correspond to the imaged objects. This may be done, e.g., by transmitting the sound waves at different angles rather than simply transmitting them in one direction (e.g., straight down), and then capture their reflections back. The returning echoes (of transmissions at different angles) are then captured, and processed (e.g., via the signal processor 240) to generate the corresponding volumetric datasets, which may in turn be used (e.g., via a 3D rendering module 242 in the signal processor 240) in creating and/or displaying volume (e.g. 3D) images, such as via the display 250. This may entail use of particular handling techniques to provide the desired 3D perception.

For example, volume rendering techniques may be used in displaying projections (e.g., 2D projections) of the volumetric (e.g., 3D) datasets. In this regard, rendering a 2D projection of a 3D dataset may comprise setting or defining a perception angle in space relative to the object being displayed, and then defining or computing necessary information (e.g., opacity and color) for every voxel in the dataset. This may be done, for example, using suitable transfer functions for defining RGBA (red, green, blue, and alpha) value for every voxel.

In various implementations in accordance with the present disclosure, the ultrasound system 200 may be configured to support fast volume contrast imaging in C-plane (VCI-C) and Omniview acquisition. In this regard, volume contrast imaging may be used (e.g., in 4D ultrasound imaging) to generate a thin 3D slice of the view being imaged and studied. In modes such as VCI-C and Omniview, the imaging is based on real-time acquisition of volumetric data (based on echo signals) for enabling rendering. In this regard, in the typical acquisition scenario a volume with both large elevation and lateral angle is acquired, but only data from a limited region of depth is displayed. In Omniview only a single plane is reconstructed out of the volume acquisition. In VCI-C the data within a region of a defined maximum depth is displayed using a rendering algorithm.

Thus, the speed of acquisition of may be increased by incorporating adaptive measures to enable reducing time between transmissions of ultrasound beams. For example, with modes such as VCI-C and Omniview, the speed of acquisition may be increased by configuring the transmissions of ultrasound beams to allow for controlled overlapping of multiple acquisition beams, as data is acquired only for depth needed (depth of plane). While in a conventional system beams are acquired in sequence, with each beam transmitted only after the echo of a prior beam has already been received and handled, the transmissions of beams in accordance with the present disclosure can be made without waiting on the echo signals as long as the successive transmissions are configured to ensure that they would not interred with one another. For example, number of beams may be increased by transmitting within each scanned plane multiple sets of beams (e.g., two or more) that are configured to be spatially and temporarily separated but overlapping—that is where a beam in each set is configured to be sufficiently spatially and temporally separated from corresponding beam(s) in the other set(s) that it can be transmitted after transmittal of beam(s) in the other set(s) but before the corresponding echoes are received.

Accordingly, in various implementations in accordance with the present disclosure, the acquisition may be performed in a linear fashion—that is plane by plane, and line by line within each plane. In some instances, MLA (multiple-line acquisition) techniques may be used to improve the acquisition speed. Nonetheless, the basic principle of a linear sweep through the volume remains the same. The acquisition speed is limited mainly by the speed of sound. Further, even though a whole volume is acquired only a small portion of the data is actually needed for display. All data closer to the ultrasound probe than the region of interest to be displayed can be ignored. In some instances, MLT (multi-line-transmit) techniques may be used to increase the acquisition speed. However, use of such techniques would require additional hardware resources to implement. The basic approach described below, on the other hand, can be done without requiring adding new hardware resources (as long as the existing processing resources are sufficient).

In an example implementation, an ultrasound system (e.g., the ultrasound system 200) may be configured to determine (e.g., via an acquisition control module 244 in the signal processor 240) number of beam sets that may be utilized during imaging operations, such as based on characteristics of the ultrasound probe being used (e.g., size, shape, curvature, etc.). For example, based on the shape, size, and curvature of the ultrasound probe (or, more specifically, the part of the ultrasound probe that is in contact with and moved over the area being scanned), the acquisition control module 244 may determine that the surface area of the ultrasound probe can be divided into 4 sectors and correspondingly four sets of beams can be used with sufficient spatial separation between beams in each of the sets as to allow interleaving during transmissions—that is transmission of ultrasound signals before echo signals of other transmitted signals has already been received.

The acquisition control module 244 may then determine time required for receiving echo signals for each transmitted beam, and timing separation between triggering of successive beams (within each set of beams and between corresponding beams in different sets of beams). The imaging functions (e.g., in the transmitter 202, the transmit beamformer 210, the receiver 218, the receive beamformer 222, etc.) may be configured and/or adjusted based on the determined beam transmission characteristics. Example use scenarios done in such manner are described below.

Figure 3:
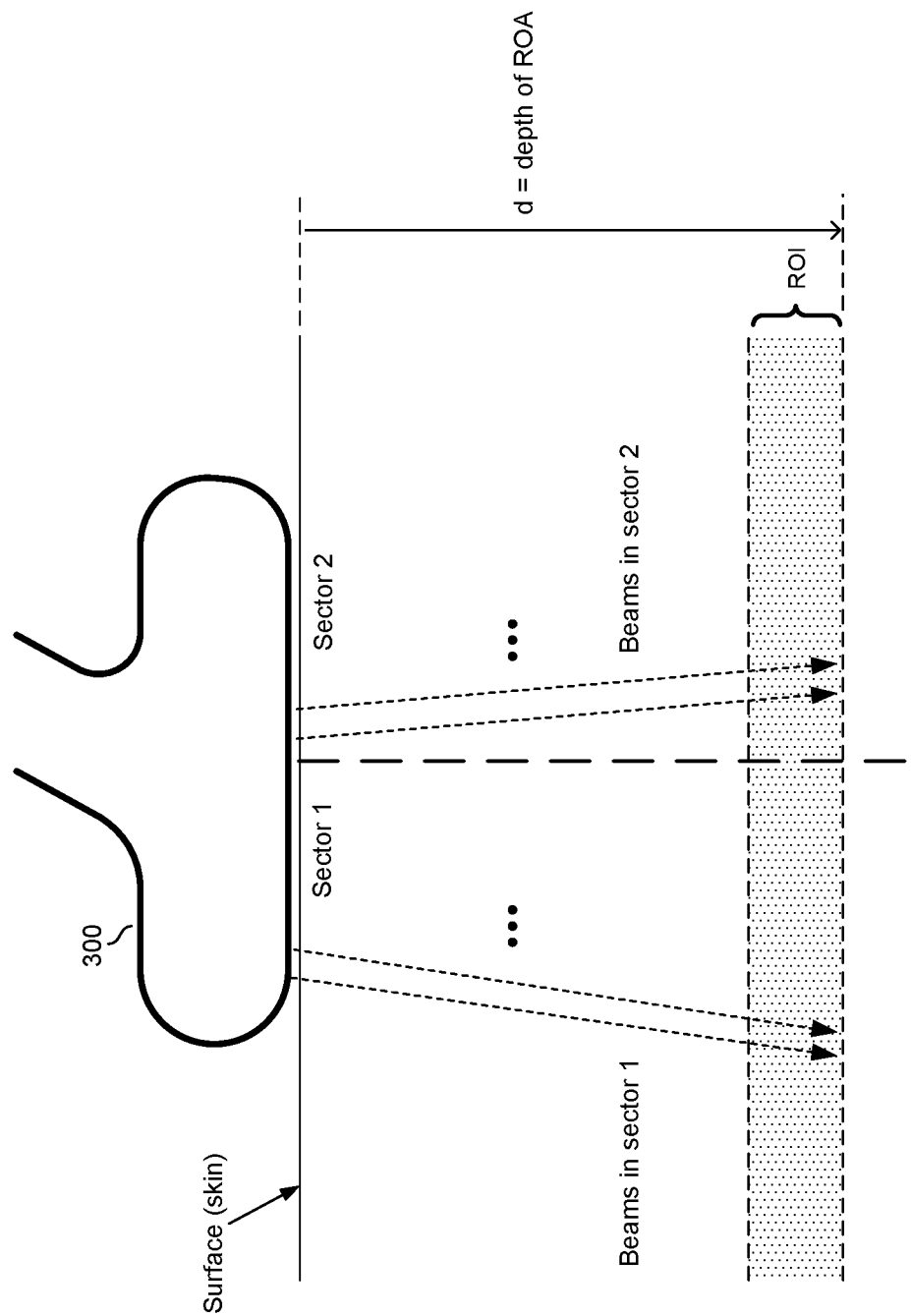
FIG. 3 is a block diagram illustrating an example configuration of ultrasound probe for supporting transmittal and capture of ultrasound beams in multiple sectors, to facilitate fast acquisition.

FIG. 3 is a block diagram illustrating an example configuration of ultrasound probe for supporting transmittal and capture of ultrasound beams in multiple sectors, to facilitate fast acquisition. Shown in FIG. 3 is an ultrasound probe 300.

The ultrasound probe 300 may comprise suitable hardware (and, in some instances, software) for emitting and capturing ultrasound signals during ultrasound scans. The ultrasound probe 300 may be portable and movable, and as such may be moved over a patient's body (or part thereof) during ultrasound imaging. The ultrasound probe 300 may be similar to the ultrasound probe 204 of FIG. 2, and may be driven and/or controlled by similar circuitry as shown in FIG. 2 (not shown in FIG. 3).

In example operation, the ultrasound probe 300 may be configured and/or controlled (e.g., by the acquisition control module 244 in the signal processor 240 of the ultrasound system 200) to perform the transmitting of ultrasound beams and capturing of corresponding echo signals based on interleaved configuration. The scanning surface of the ultrasound probe 300 may divided into a plurality of sectors (e.g., two sectors, right and left, in the particular configuration illustrated in FIG. 3), with a corresponding plurality of sets of beams. In this regard, the number (and disposition) of the sectors may be determined, based on characteristics of the ultrasound probe 300 (e.g., size, shape, curvature, etc.), to ensure optimal spatial separation between the corresponding sets of beams (e.g., between beams used in sector 1 and beams use din sector 2, as shown in FIG. 3).

The transmission of the beams may then be configured, based on the determined sectors as well as other factors that may be deemed pertinent to the timing of such transmissions. In this regard, the number of beams may be transmitted within each sectors, and the manner by which the beams are transmitted (e.g., relative timing for each beam with respect to other beams within the same set/sector and with respect to beams in other set(s)/sector(s)) may be adaptively configured to ensure optimal performance—that is the highest speed of acquisition possible without any (or with negligible) interference between the beams during capturing and handling of echo signals. For example, the transmission of the beams, particularly timing of transmission and spacing between beams, may be set or selected based on the best temporal and spatial separation (and thus interleaving of the beams) possible for achieving the largest increase possible in speed of acquisition.

For example, the spacing between the beams may be dependent on the sectors. In this regard, the configuration of the sectors is presumed to ensure acceptable spatial separation between the beams in different sets. As for the timing of the transmissions, the timing of when to emit each beam may be determined as to ensure sufficient temporal separation (e.g., acceptable overlap between the beams, where one beams is emitted before an echo of another has been received) may be done in adaptive manner. For example, the timing may be determined based on number of sectors/sets, a distance associated with the target plane (e.g., thickness of the region of interest (ROI) and/or maximum depth of the ROI), etc. An example timing profile is shown and described in FIG. 4.

Figure 4:
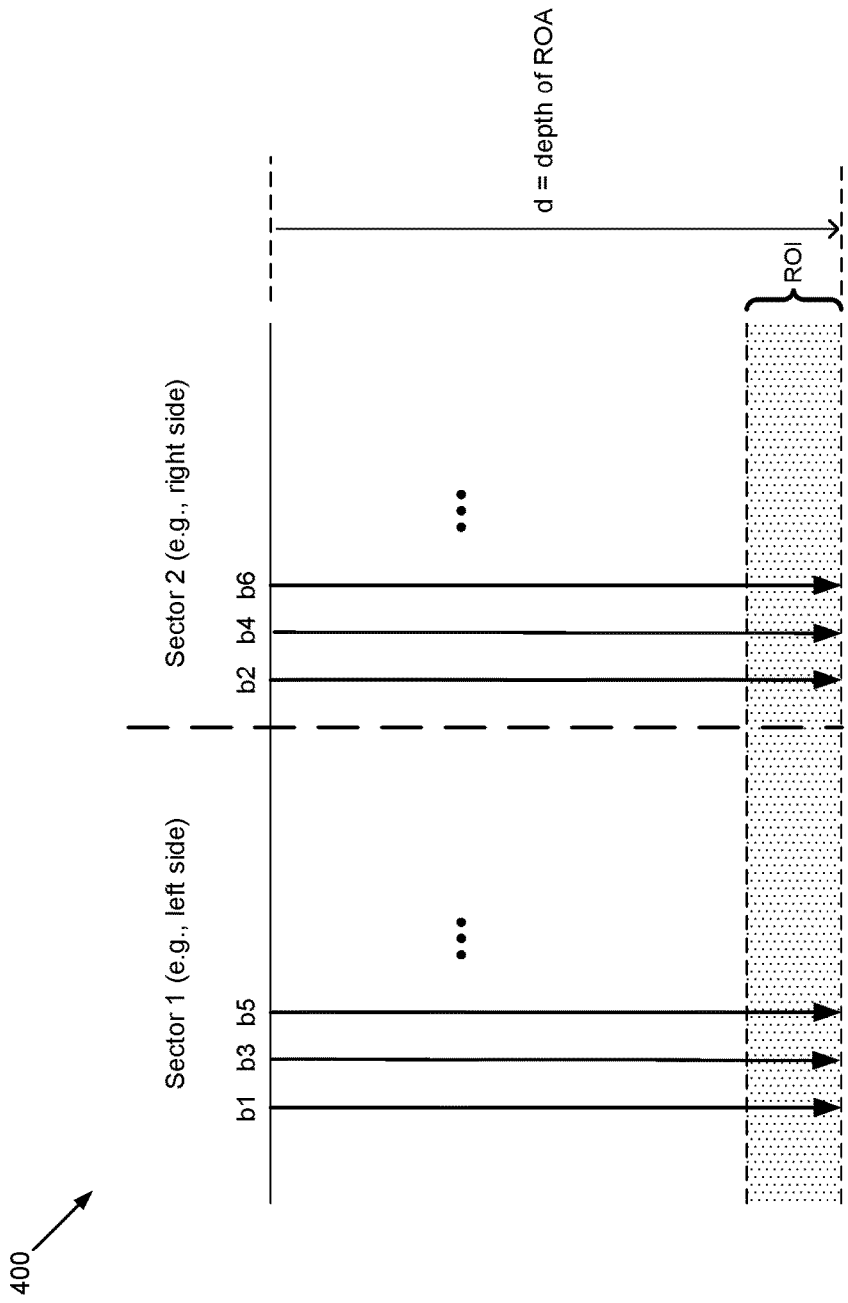
FIG. 4 is a timing diagram illustrating an example beam transmittal profile for an ultrasound probe that supports multiple beam sectors, to facilitate fast acquisition.

FIG. 4 is a timing diagram illustrating an example beam transmittal profile for an ultrasound probe that supports multiple beam sectors, to facilitate fast acquisition. Shown in FIG. 4 is timing diagram 400.

The timing diagram 400 may correspond to timing profile when utilizing temporal and spatial interleaving in an example use scenario of the ultrasound probe 300, particularly where two sectors (and thus two sets of beams) are used. In this regard, as shown in the timing diagrams 400, each of the two sets (for sector 1 and sector 2, respectively) may comprise a sequence of beams—particularly beams b1, b3, b5, . . . for sector 1, and beams b2, b,4, b6, . . . for sector 2. The sectors are configured such that the corresponding beams in the different sets are presumed to have sufficient spatial separation therebetween as to allow for overlap—that is beams in one sets can be emitted before echoes for beams of the other sets are received.

With respect to the timing of the beam transmission, this may be determined based on such factors as number of sectors, depth of region of interest (being imaged), etc. Thus, assuming that $\Delta t$ is the time needed for the acquisition of beams for the desired ROI at a particular maximum depth of d (e.g., $\Delta t \approx 2d/c$, where c is speed of sound) then once a beam is transmitted in a particular set (e.g., b1 in sector 1), the acquisition of a beam in the other set (e.g., b2 in sector 2) can then be may started (by transmitting b2) after a delay that can be less than the time needed to receive the echo of the first beam (e.g., after $\Delta t/2$) The set delay for triggering transmission of beams in other sets as describe in this implementation is based on number of sectors. Thus, assuming 3 sectors, the delay can be $\Delta t/3$). The disclosure is not so limited, however, and triggering transmission of beams in other sets may be offset adaptively in other ways.

Accordingly, for the particular example shown in FIG. 4, this gives a (simplified) timing sequence as shown in the following table (assuming time t starts at 0 with transmission of the first beam):

TABLE 1

| Time | Action |
| --- | --- |
| t = 0 | Transmit b1 |
| t = $\Delta t/2$ | Transmit b2 |
| t = $\Delta t$ | Transmit b3, immediately followed by Receive echo of b1 |
| t = 3/2 * $\Delta t$ | Transmit b4, immediately followed by Receive echo of b2 |
| t = 2 * $\Delta t$ | Transmit b5, immediately followed by Receive echo of b3 |
| t = 5/2 * $\Delta t$ | Transmit b6, immediately followed by Receive echo of b4 |
| . . . | . . . |

The above timing sequence is a simplified one that is based on the estimated time of acquisition ($\Delta t$) for acquiring echoes of transmitted signals for particular distance. In this regard, for maximum depth of d for the region of interest (ROI), which would result in $\Delta t \approx 2d/c$. It should be noted here that the time of acquisition ($\Delta t$) may include, in addition, to the time needed for the echo signals to travel back to the probe (that is 2d/c for ROI with maximum depth of d) some additional time that is needed for the actual capture and initial processing of the echo signals.

When configured in the manner described above—that is with the overlapping beams (beams in different sets) transmitted with temporal separation based on the timing sequence, and spatial separation from the spacing between the emission points in the probe, there would be minimal interference between the beams, and they should not affect one another. In this regard, cross-talk between the overlapping beams will be limited due to the spatial and/or temporal separation of the beams. As noted above, while this particular example is described based on two sets of beams (and two sectors in the probe), the disclosure is not so limited. Thus, in some instances more than two beam sets can be used parallel. This may be possible where the geometry of the probe (e.g., micro-curved probes) may be deemed to permit multiple overlapping beams (e.g., 3 or more sets).

In some implementations, the approach described above may be extended to 2D scanning. In this regard, use of overlapping beams may be done with 2D arrays, for which it would be very difficult to provide MLT (multi-line-transmit) transmit and receive hardware. In such case, overlapping beams may be separated not only in azimuth but also in elevation, which may allow for overcoming possible crosstalk issues.

Figure 5:
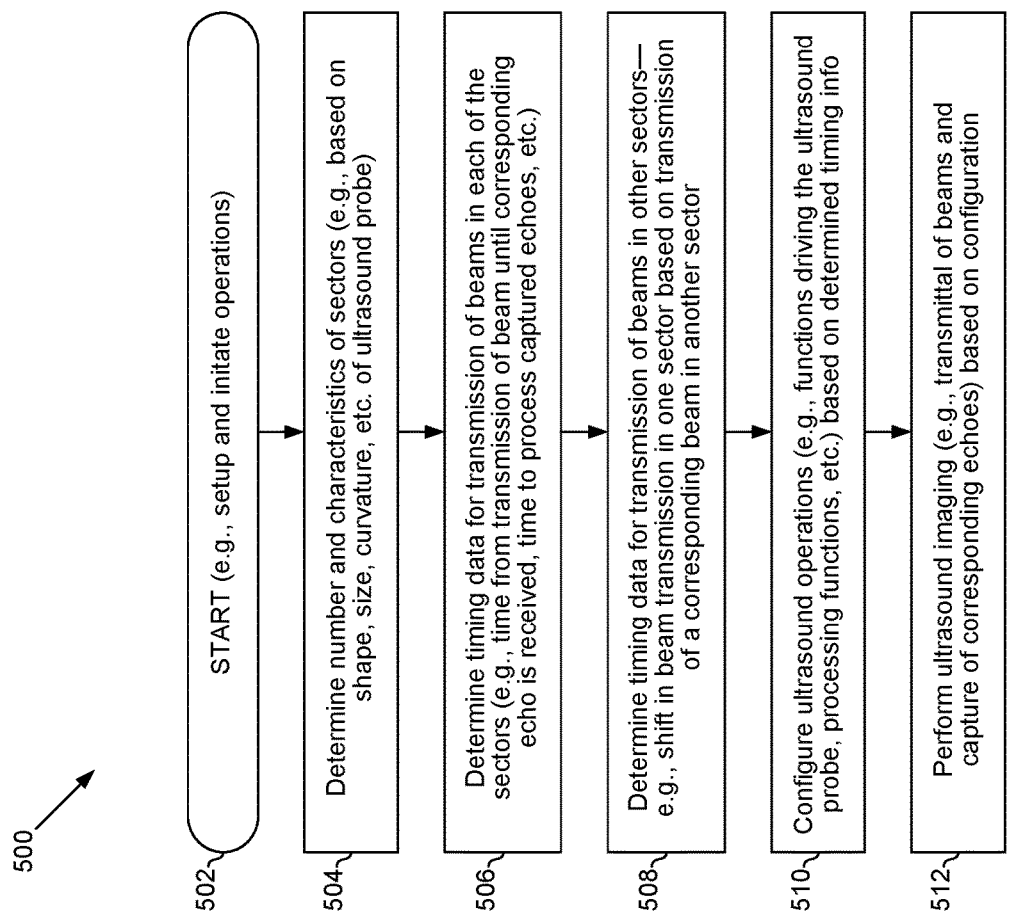
FIG. 5 illustrates a flowchart of example steps that may be performed for fast volume contrast imaging in C-plane (VCI-C) and Omniview acquisition.

FIG. 5 illustrates a flowchart of example steps that may be performed for fast volume contrast imaging in C-plane (VCI-C) and Omniview acquisition. Shown in FIG. 5 is flow chart 500, comprising a plurality of example steps (represented as blocks 502-512), which may be performed in a suitable system (e.g., system 200 of FIG. 2) for performing fast volume contrast imaging in C-plane (VCI-C) and Omniview acquisition.

In start step 502, the system may be setup, and operations may initiate.

In step 504, number and characteristics of sectors may be determined (e.g., based on shape, size, curvature, etc. of ultrasound probe).

In step 506, timing data for transmission of beams in each of the sectors (e.g., time from transmission of beam until corresponding echo is received, time to process captured echoes, etc.) may be determined.

In step 508, timing data for transmission of beams in other sectors (e.g., shift in beam transmission in one sector based on transmission of a corresponding beam in another sector, etc.) may be determined.

In step 510, ultrasound operations (e.g., functions driving the ultrasound probe, processing functions, etc.) may be configured based on determined timing info.

In step 512, ultrasound imaging operations may be performed based on that configuration.

As utilized herein the terms "circuits" and "circuitry" refer to physical electronic components (e.g., hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. In other words, "x and/or y" means "one or both of x and y." As another example, "x, y, and/or z" means any element of the seven-element set {(x), (y), (z), (x, y), (x, z), (y, z), (x, y, z)}. In other words, "x, y and/or z" means "one or more of x, y, and z." As utilized herein, the terms "block" and "module" refer to functions than can be performed by one or more circuits. As utilized herein, the term "exemplary" means serving as a non-limiting example, instance, or illustration. As utilized herein, the terms "for example" and "e.g.," set off lists of one or more non-limiting examples, instances, or illustrations. As utilized herein, circuitry is "operable" to perform a function whenever the circuitry comprises the necessary hardware (and code, if any is necessary) to perform the function, regardless of whether performance of the function is disabled or not enabled (e.g., by some user-configurable setting, a factory trim, etc.).

Other embodiments of the invention may provide a non-transitory computer readable medium and/or storage medium, and/or a non-transitory machine readable medium and/or storage medium, having stored thereon, a machine code and/or a computer program having at least one code section executable by a machine and/or a computer, thereby causing the machine and/or computer to perform the processes as described herein.

Accordingly, the present disclosure may be realized in hardware, software, or a combination of hardware and software. The present invention may be realized in a centralized fashion in at least one computing system, or in a distributed fashion where different elements are spread across several interconnected computing systems. Any kind of computing system or other apparatus adapted for carrying out the methods described herein is suited. A typical combination of hardware and software may be a general-purpose computing system with a program or other code that, when being loaded and executed, controls the computing system such that it carries out the methods described herein. Another typical implementation may comprise an application specific integrated circuit or chip.

Various embodiments in accordance with the present disclosure may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. An ultrasound system, comprising:
   an ultrasound probe that is operable to transmit ultrasound signals and receive echo ultrasound signals; and
   processing circuitry that is operable to increase acquisition speed during one or more particular ultrasound imaging modes by:
   dividing an area subject to transmittal of ultrasound signals, and capture of corresponding echo ultrasound signals, by said ultrasound probe into a plurality of sectors;
   triggering transmitting of one or more beams in a first one of said plurality of sectors; and
   triggering transmittal of one or more beams in at least a second one of said plurality of sectors;
   wherein:
   each of said one or more beams transmitted in said second one of said plurality of sectors is triggered such that it is transmitted after transmitting of a corresponding beam in said first one of said plurality of sectors and before echo of said corresponding beam in said first one of said plurality of sectors is received.

2. The ultrasound system of claim 1, wherein said processing circuitry is operable to:
   determine a timing delay between transmittal of each beam in said first one of said plurality of sectors and reception of an echo of said beam; and
   determine, based on said determined timing delay and number of sectors in said plurality of sectors, a timing shift for transmitting a corresponding beam on at least said second one of said plurality of sectors.

3. The ultrasound system of claim 2, wherein said processing circuitry is operable to determine said timing delay based on speed of sound and a distance associated with desired region of interest, said distance comprising at least one of a distance associated with desired region of interest, said distance comprising at least one of a thickness of said region of interest and/or a depth of said region of interest.

4. The ultrasound system of claim 1, wherein said processing circuitry is operable to configure said plurality of sectors such that beams transmitted in each of said plurality of sectors are spatially separated in relation to one another.

5. The ultrasound system of claim 1, wherein said processing circuitry is operable to configure said plurality of sectors based on geometric characteristics of said ultrasound probe.

6. The ultrasound system of claim 5, wherein said geometric characteristics comprise one or more of size, shape, and curvature.

7. The ultrasound system of claim 1, wherein said one or more particular ultrasound imaging modes comprise volume contrast imaging in C-plane (VCI-C) and Omniview.

8. A method, comprising:
   increasing acquisition speed, in an ultrasound device, during one or more particular ultrasound imaging modes by:
   dividing an area, subject to transmittal of ultrasound signals and capture of corresponding echo ultrasound signals by an ultrasound probe, into a plurality of sectors;
   triggering transmitting of one or more beams in a first one of said plurality of sectors; and
   triggering transmittal of one or more beams in at least a second one of said plurality of sectors;
   wherein:
   each of said one or more beams transmitted in said second one of said plurality of sectors is triggered such that it is transmitted after transmitting of a corresponding beam in said first one of said plurality of sectors and before echo of said corresponding beam in said first one of said plurality of sectors is received.

9. The method of claim 8, comprising:
   determining a timing delay between transmittal of each beam in said first one of said plurality of sectors and reception of an echo of said beam; and
   determining, based on said determined timing delay and a number of sectors in said plurality of sectors, a timing shift for transmitting a corresponding beam in at least said second one of said plurality of sectors.

10. The method of claim 9, comprising determining said timing delay based on speed of sound and a distance associated with desired region of interest, said distance comprising at least one of a thickness of said region of interest and/or a depth of said region of interest.

11. The method of claim 8, comprising configuring said plurality of sectors such that beams transmitted in each of said plurality of sectors are spatially separated in relation to one another.

12. The method of claim 8, comprising configuring said plurality of sectors based on geometric characteristics of said ultrasound probe.

13. The method of claim 12, wherein said geometric characteristics comprise one or more of size, shape, and curvature.

14. The method of claim 8, wherein said one or more particular ultrasound imaging modes comprise volume contrast imaging in C-plane (VCI-C) and Omniview.

15. A non-transitory computer readable medium having stored thereon, a computer program having at least one code section, said at least one code section being executable in an ultrasound device for causing said ultrasound device to increase acquisition speed, during one or more particular ultrasound imaging modes, by performing one or more steps comprising:
   dividing an area subject to transmittal of ultrasound signals, and capture of corresponding echo ultrasound signals, by said ultrasound probe into a plurality of sectors;
   triggering transmitting of one or more beams in a first one of said plurality of sectors; and
   triggering transmittal of one or more beams in at least a second one of said plurality of sectors;
   wherein:
      each of said one or more beams transmitted in said second one of said plurality of sectors is triggered such that it is transmitted after transmitting of a corresponding beam in said first one of said plurality of sectors and before echo of said corresponding beam in said first one of said plurality of sectors is received.

16. The non-transitory computer readable medium of claim 15, the one or more steps further comprising:
   determining a timing delay between transmittal of each beam in said first one of said plurality of sectors and reception of an echo of said beam; and
   determining, based on said determined timing delay and a number of sectors in said plurality of sectors, a timing shift for transmitting a corresponding beam in at least said second one of said plurality of sectors.

17. The non-transitory computer readable medium of claim 16, the one or more steps further comprising determining said timing delay based on speed of sound and a distance associated with desired region of interest, said distance comprising at least one of a thickness of said region of interest and/or a depth of said region of interest.

18. The non-transitory computer readable medium of claim 15, the one or more steps further comprising configuring said plurality of sectors such that beams transmitted in each of said plurality of sectors are spatially separated in relation to one another.

19. The non-transitory computer readable medium of claim 15, the one or more steps further comprising configuring said plurality of sectors based on geometric characteristics of said ultrasound probe.

20. The non-transitory computer readable medium of claim 19, wherein said geometric characteristics comprise one or more of size, shape, and curvature.

21. The non-transitory computer readable medium of claim 15, wherein said one or more particular ultrasound imaging modes comprise volume contrast imaging in C-plane (VCI-C) and Omniview.

* * * * *